(12) United States Patent
List et al.

(10) Patent No.: US 7,683,191 B2
(45) Date of Patent: Mar. 23, 2010

(54) ORGANIC SALTS AND METHOD FOR PRODUCING CHIRAL ORGANIC COMPOUNDS

(75) Inventors: Benjamin List, Mülheim an der Ruhr (DE); Sonja Mayer, Mülheim an der Ruhr (DE); Martin Nolwenn, Mülheim an der Ruhr (DE); Wang Xingwang, Mülheim an der Ruhr (DE)

(73) Assignee: Studiangesellschaft Kohle mbH, Molhelm an der Ruhr (DE)

( * ) Notice: Subject to any disclaimer, the term of this patent is extended or adjusted under 35 U.S.C. 154(b) by 0 days.

(21) Appl. No.: 12/280,821

(22) PCT Filed: Feb. 27, 2007

(86) PCT No.: PCT/DE2007/000365

§ 371 (c)(1), (2), (4) Date: Aug. 27, 2008

(87) PCT Pub. No.: WO2007/098741

PCT Pub. Date: Sep. 7, 2007

(65) Prior Publication Data

US 2009/0030216 A1  Jan. 29, 2009

(30) Foreign Application Priority Data

Mar. 1, 2006 (DE) ........................ 10 2006 009 518

(51) Int. Cl.
*C07D 301/19* (2006.01)
(52) U.S. Cl. .................. 549/529; 502/150; 549/531; 560/231; 568/351; 568/433; 568/459
(58) Field of Classification Search .............. 502/162, 502/164, 167, 168, 150; 540/546; 549/348, 549/523, 529; 562/231; 568/351, 433, 459
See application file for complete search history.

(56) References Cited

FOREIGN PATENT DOCUMENTS

| | | |
|---|---|---|
| EP | 1 038 877 A1 | 9/2000 |
| JP | 2002 069066 A | 3/2002 |
| WO | 2005 037765 | 4/2005 |
| WO | 2006 017148 | 2/2006 |

OTHER PUBLICATIONS

Llewellyn et al, "Synthesis of a library of chiral α-amino acid-based borate counteranions and their application to copper catalyzed olefin cyclopropanation"; Tetrahedron: Asymmetry 16 (2005), pp. 1789 1799.
Carter et al; "Towardsphase-transfer catalysts with a chiral anion: inducing asymmetry in the reactions of cations"; Tetrahedron: Asymmetry 14, (2003), pp. 1995-2004.
Hanamoto, et al; "Asymmetric hetero diels-alder reaction catalyzed by chiral ytterbium(III) phosphate {Yb[(R)-(-)-BNP]3}: Remarkable ligand effect on the enantioselectivity"; Synlett 79, Jan. 1997, pp. 79-80.
Inanaga et al; "Achiral and chiral lanthanide(III) salts of superacids as novel lewis acid and catalysts in organic synthesis"; New J. Chem. 1995, 19, pp. 707-712.
Rueping et al; "Enantioselective Brønsted acid catalyzed transfer hydrogenation: organocatalytic reduction of imines"; Organic letters, (2005), vol. 7, No. 17, pp. 3781-3783.
Akiyama et al; "Enantioselective Mannich-type reaction catalyzed by a chiral Brønsted acid"; Angew. Chem,. Int. Ed. 2004, vol. 43, pp. 1566-1568.
Uraguchi et al; "Chira; Brønsted acid-catalyzed direct Mannich reactions via electrophilic activation"; J. Am. Chem. Soc., 2004, vol. 126, pp. 5356-5357.
Machado, et al; "Synthesis and characterization of chiral imidazolium salts"; Synthesis 2005, No. 15, pp. 2473-2475.
Rueping et al; "Brønsted acid catalysis: organocatalytic hydrogenation of imines"; Synlet 2005, No. 15, pp. 2367-2369.
Yang, et al; "A metal-free tranfer hydtogenation: organocatalytic conjugate reduction of α, β-unsaturated aldehydes"; Angew. Chem. Int. Ed. 2004, vol. 43, pp. 6660-6662.

*Primary Examiner*—Bernard Dentz
*Assistant Examiner*—David E Gallis
(74) *Attorney, Agent, or Firm*—Norris McLaughlin & Marcus, P.A

(57) ABSTRACT

The invention relates to a method for producing chiral organic compounds by asymmetric catalysis, using ionic catalysts comprising a chiral catalyst anion. The claimed method is suitable for reactions which are carried out over cationic intermediate stages, such as iminium ions or acyl pyridinium ions. The invention enables the production of chiral compounds with high ee values, that until now could only be obtained by means of costly purification methods.

6 Claims, No Drawings

ORGANIC SALTS AND METHOD FOR PRODUCING CHIRAL ORGANIC COMPOUNDS

This application is a 371 of PCT/DE2007/000365, filed Feb. 27, 2007, which claims foreign priority benefit under 35 U.S.C. 119 of the German Patent Application No. 10 2006 009 518.9 filed Mar. 1, 2006.

The present invention relates to a process for preparing chiral organic compounds.

Many chemical transformations proceed via ionic intermediates and transition states. Such polar reactions are influenced by the particular counterion. For example, the course of reactions of carbanions can be modified by adding suitable cationic substances. This principle is well known in so-called phase transfer catalysis, in which the reactions of enolates and similar anionic substrates with various electrophiles can be catalyzed asymmetrically.

D. B. Llewellyn, B. A. Arndtsen describe, in *Tetrahedron Asymmetry* 2005, 16, 1789-1799, reactions with reversed polarization, but no acceptable enantioselectivities were realized.

It was accordingly an object of the present invention to provide a process for preparing chiral organic compounds, that to broaden the spectrum of chiral compounds with high ee values, preferably >50%, preparable by synthesis, and also to enable the synthesis of those enantiomers which can be obtained only as enantiomer mixtures according to the prior art.

The present invention accordingly provides a process for preparing chiral organic compounds by asymmetric catalysis using ionic catalysts, which is characterized in that the catalyst anion of the ionic catalyst is chiral.

It has been found that, surprisingly, it is possible by the process according to the invention to prepare chiral compounds in virtually enantiomerically pure form, in most cases with an ee of more than 90%, said compounds being obtainable only by complicated purification methods from the state. One example of this is the highly enantioselective reduction of citral to the perfume ingredient citronellal.

The process according to the invention is mediated by salt catalysts which are composed of a chiral or achiral cation and a chiral anion. In a preferred embodiment, enantiomerically enriched catalysts, i.e. catalysts which have an excess of one enantiomer, or enantiomerically pure compounds are used. These catalysts can be prepared, for example, by reacting a chiral or achiral base with a chiral acid. Alternatively, the catalytic salts can also be prepared in situ from acid and base or by means of other common methods known to those skilled in the art. The chiral or achiral cation is preferably an ammonium compound. Typical examples of inventive catalysts are shown in scheme 1.

Scheme 1. Selection of possible catalysts for processes according to the invention.

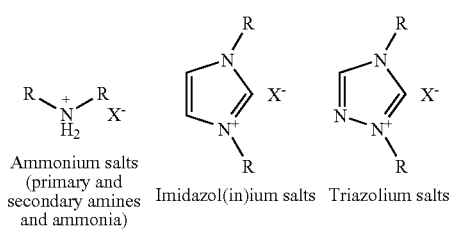

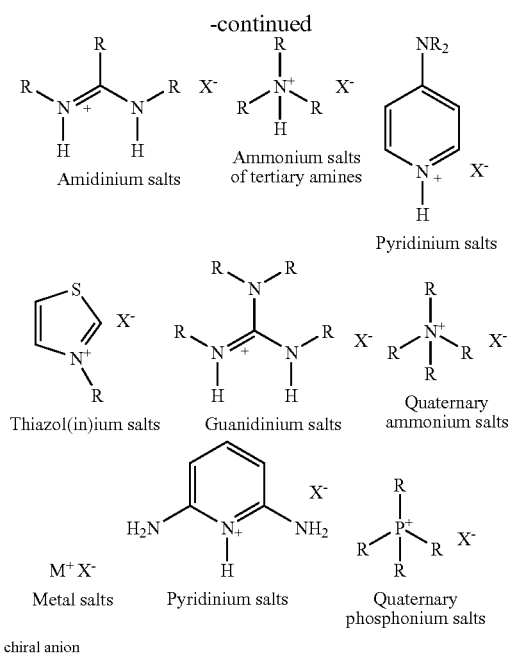

$X^-$ = chiral anion

The possible catalytic salts catalyze reactions which proceed via cationic intermediates. Such intermediates may, for example, be: iminium ions, N-acyliminium ions, acylammonium ions, phosphonium ions, sulfonium ions, oxonium ions or carbenium ions.

The process according to the invention suitable for preparing a multitude of chiral compounds is not limited to any specific reaction type. An important class of possible reactions is that of nucleophilic additions and cycloadditions of ($\alpha,\beta$-unsaturated) carbonyl compounds which proceed via cationic iminium ion precursors, and are catalyzed by salts of primary and secondary amines (scheme 2). These include Diels-Alder reactions, 1,3-dipolar cycloadditions, conjugated additions, epoxidations, cyclopropanations, transfer hydrogenations, Mukayama-Michael additions and Knoevenagel reactions. However, the principle is not restricted to these reactions.

Such reactions have already been catalyzed asymmetrically. However, the catalyst used was always a salt which is composed of a chiral amine (as a base) and an (a) chiral acid (or the chiral amine alone). This invention, in contrast, provides for the use of salts of achiral (or chiral) amines with chiral acids.

Scheme 2. Selection of possible reactions which can be catalyzed asymmetrically by the process according to the invention and proceed via iminium ions.

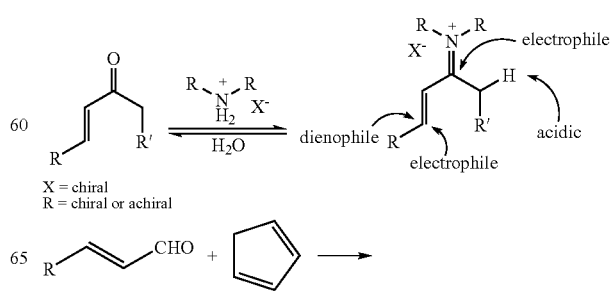

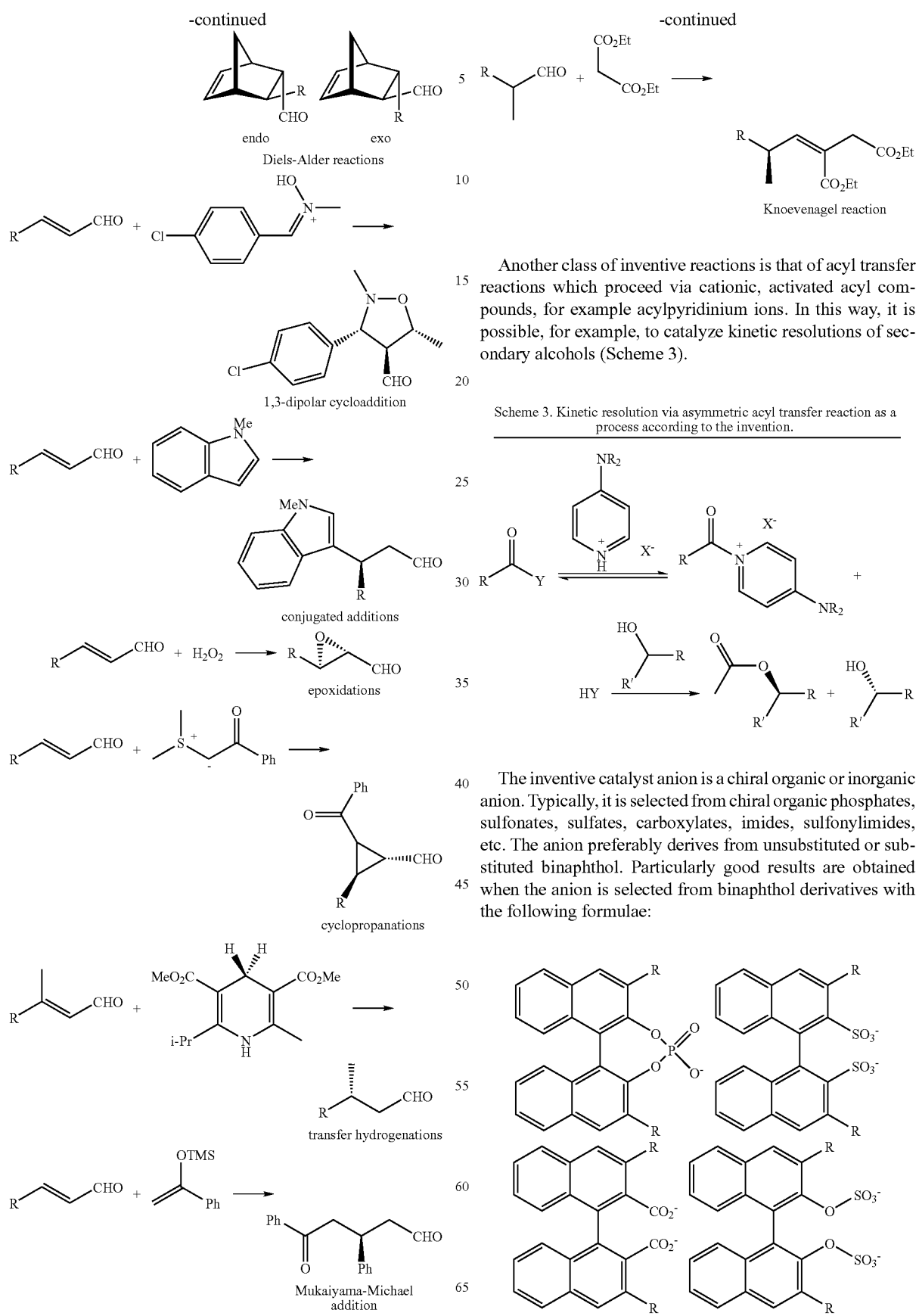

Another class of inventive reactions is that of acyl transfer reactions which proceed via cationic, activated acyl compounds, for example acylpyridinium ions. In this way, it is possible, for example, to catalyze kinetic resolutions of secondary alcohols (Scheme 3).

Scheme 3. Kinetic resolution via asymmetric acyl transfer reaction as a process according to the invention.

The inventive catalyst anion is a chiral organic or inorganic anion. Typically, it is selected from chiral organic phosphates, sulfonates, sulfates, carboxylates, imides, sulfonylimides, etc. The anion preferably derives from unsubstituted or substituted binaphthol. Particularly good results are obtained when the anion is selected from binaphthol derivatives with the following formulae:

-continued

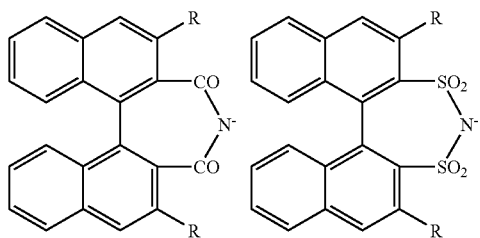

in which

R is hydrogen, substituted or unsubstituted alkyl or substituted or unsubstituted aryl.

The cationic counterion used for the chiral anion used in accordance with the invention may be any cation. The cation is preferably selected from alkali metal ions and ammonium ions, particular preference being given to ammonium ions.

The term "alkyl" used means a linear, branched or cyclic hydrocarbon radical which has typically from 1 to 30, preferably from 1 to 24 carbon atoms, and especially from 1 to 6 carbon atoms, such as methyl, ethyl, n-propyl, isopropyl, n-butyl, isobutyl, t-butyl, octyl, decyl, etc., but also cycloalkyl groups such as cyclopentyl, cyclohexyl, etc. The hydrocarbon radicals have preferably from 1 to 18, especially from 1 to 12 carbon atoms.

The aryl groups used in the context of the present invention are aromatic ring systems having 5 to 30 carbon atoms and optionally heteroatoms such as N, O, S, P, Si, in the ring, where the rings may be simple or multiple ring systems, for example fused ring systems or rings bonded to one another via single bonds or multiple bonds. Examples of aromatic rings are phenyl, naphthyl, biphenyl, diphenyl ether, diphenylamine, benzophenone and the like. Substituted aryl groups have one or more substituents. Examples of heteroalkyl groups are alkoxyaryl, alkylsulfanyl-substituted alkyl, N-alkylated aminoalkyl and the like. Examples of heteroaryl substituents are pyrrolyl, pyrrolidinyl, pyridinyl, quinolinyl, indolyl, pyrimidinyl, imidazolyl, 1,2,4-triazolyl, tetrazolyl, and the like. Examples of heteroatom-containing alicyclic groups include pyrrolidino, morpholino, piperazino, piperidino, etc.

Possible substituents that the aforementioned groups may have include OH, F, Cl, Br, I, CN, $NO_2$, NO, $SO_2$, $SO_3$—, amino, —COOH, —COO($C_1$-$C_6$-alkyl), mono- and di-($C_1$-$C_{24}$-alkyl)-substituted amino, mono- and di-($C_5$-$C_{20}$-aryl)-substituted amino, imino, which may in turn be substituted, for example $C_1$-$C_6$-alkyl, aryl, and phenyl. Especially the cyclic radicals may also have $C_1$-$C_6$-alkyl groups as substituents.

Particularly suitable anions have been found to be those which derive from binaphthol (e.g. phosphates, sulfonates, sulfates, carboxylates, imides, sulfonylimides, see Scheme 4). However, the anions are in no way restricted to these structures.

Scheme 4. Selection of possible inventive anions.

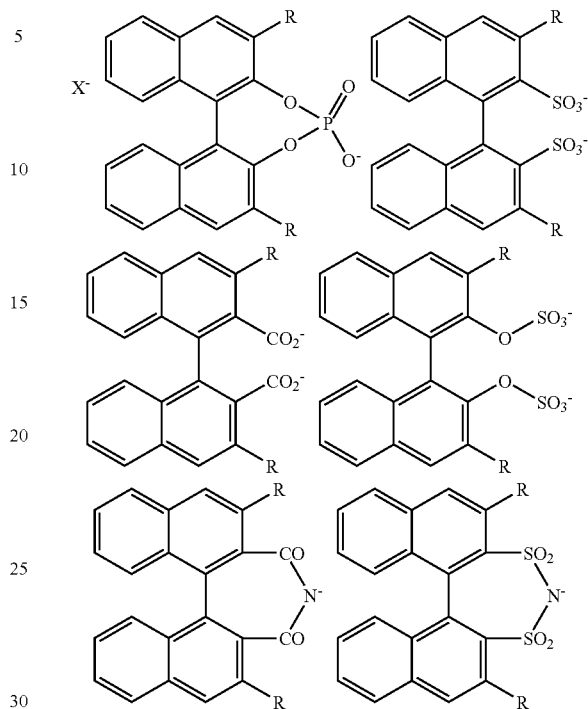

The reaction conditions which exist for performance of the process according to the invention depend essentially on the reaction type selected and can be established immediately by the person skilled in the art.

EXAMPLES

Primary and secondary amine salts of chiral phosphoric acids highly enantioselectively catalyze the transfer hydrogenation of alpha,beta-unsaturated carbonyl compounds with the aid of Hantzsch esters (Scheme 5).

Scheme 5. Transfer hydrogenation as an example.

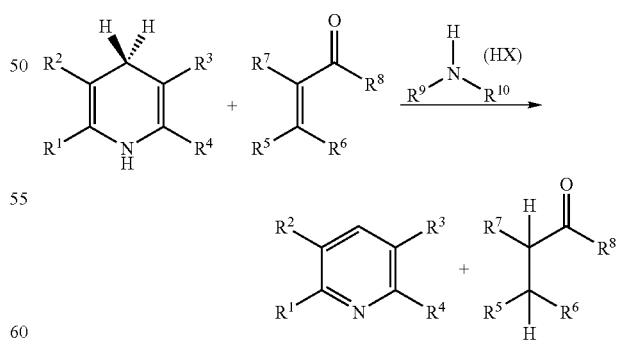

For instance, the salt 1, in the presence of the Hantzsch ester 4, catalyzes the highly enantioselective transfer hydrogenation of various alpha,beta-unsaturated aldehydes (2) (Scheme 6). Further catalytic salts for the enantioselective transfer hydrogenation are shown in Schemes 7-9.

Scheme 6.
Inventive highly enantioselective transfer hydrogenations.

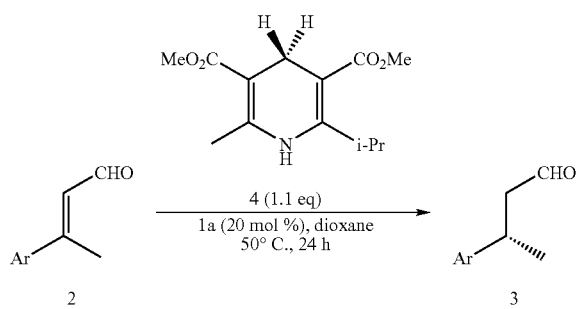

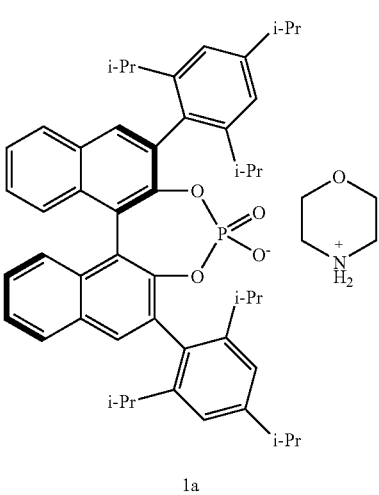

1a

| | Ar | Yield | ee |
|---|---|---|---|
| (a) | 4-MeC$_6$H$_4$ | 87% | 96% |
| (b) | 4-NCC$_6$H$_4$ | 84% | 97% |
| (c) | 4-NO$_2$C$_6$H$_4$ | 90% | 98% |
| (d) | 4-BrC$_6$H$_4$ | 67% | 96% |
| (e) | 4-F$_3$CC$_6$H$_4$ | 63% | 98% |
| (f) | 2-naphthyl | 72% | 99% |

Scheme 7. Highly enantioselective transfer hydrogenation. Further examples of morpholine salts.

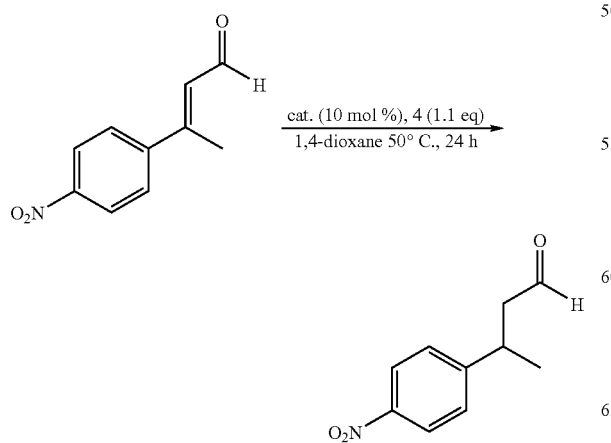

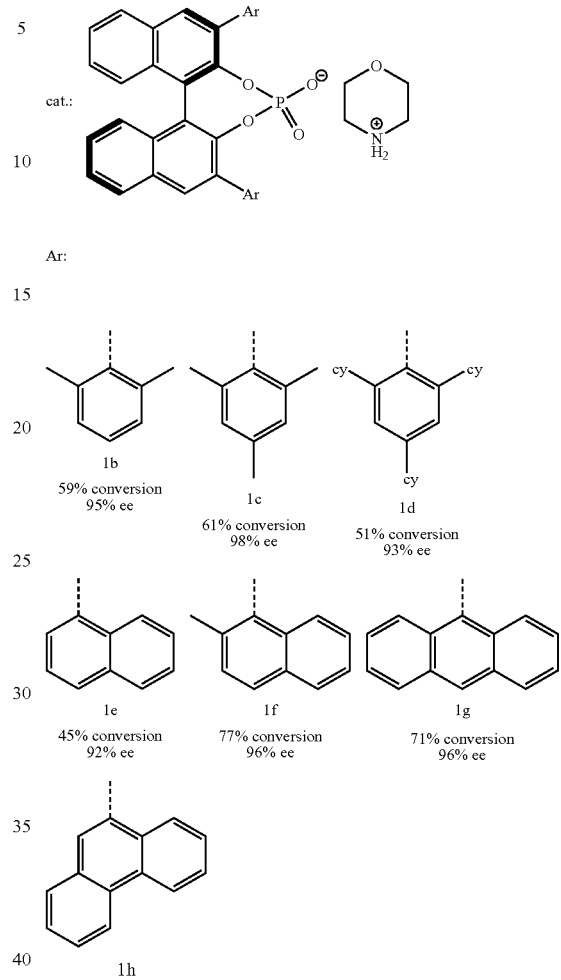

Scheme 8. Highly enantioselective transfer hydrogenation. Further examples of various 3,3'-bis(2,4,6-triisopropylphenyl)-1,1'-binaphthyl-2,2'-diyl hydrogenphosphate salts.

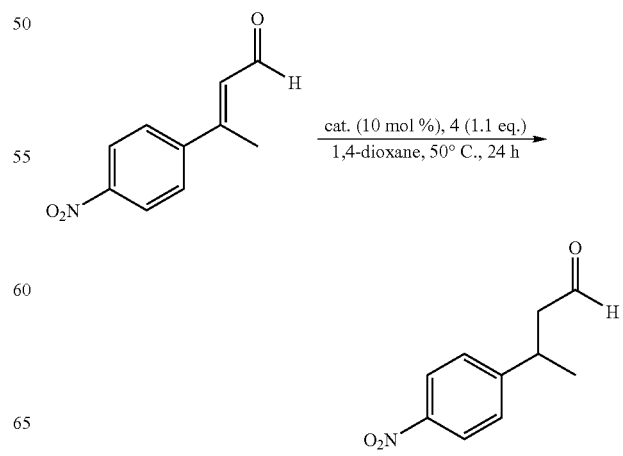

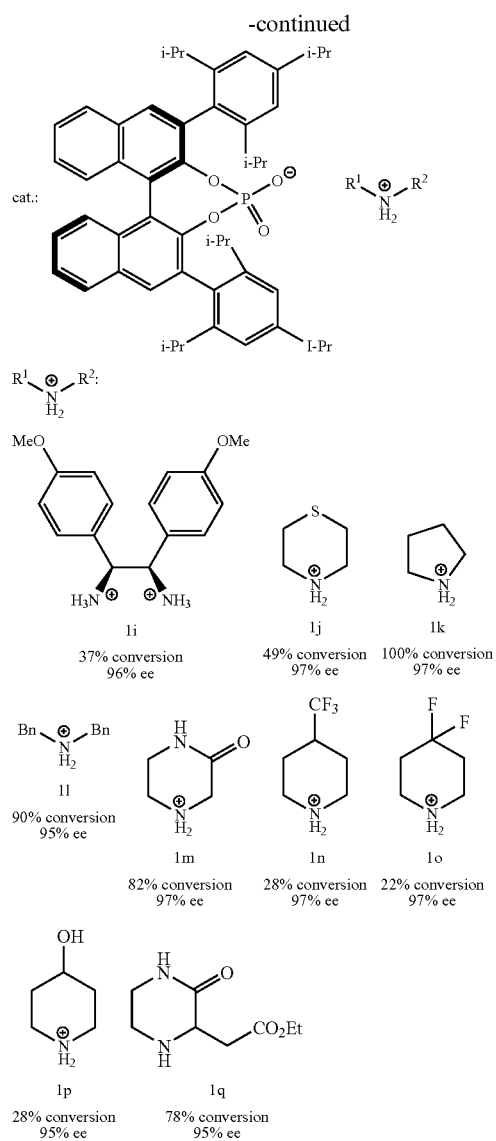
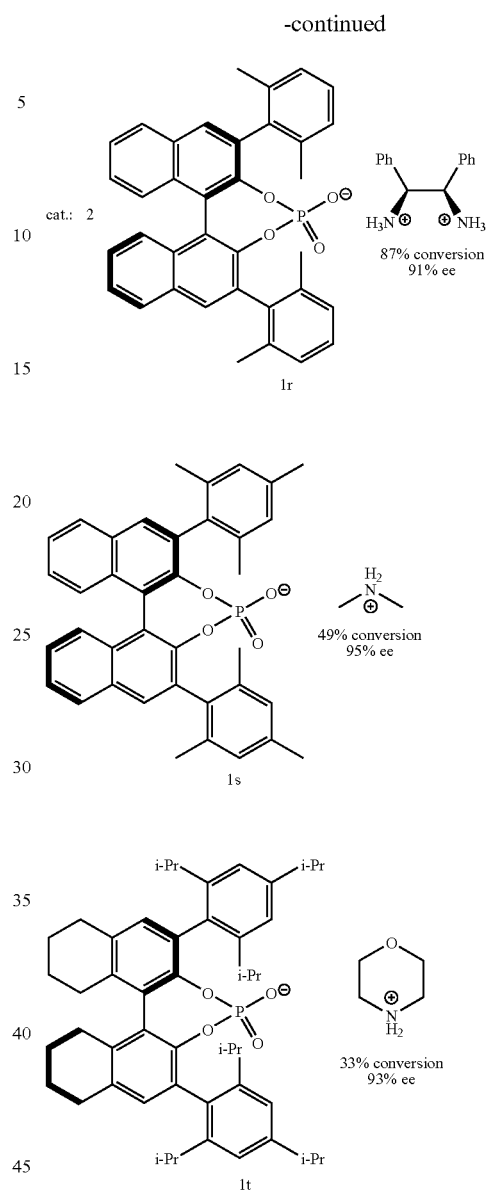
Scheme 9. Highly enantioselective transfer hydrogenation. Further examples.
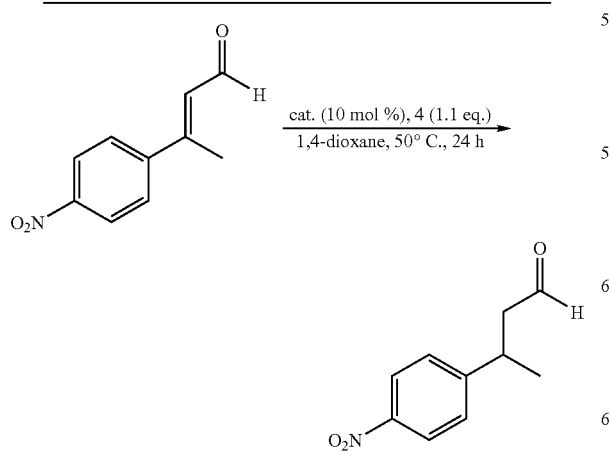
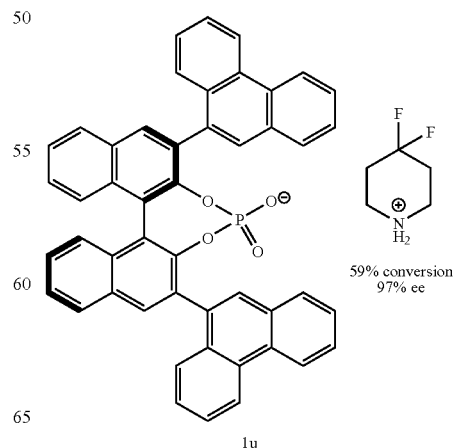

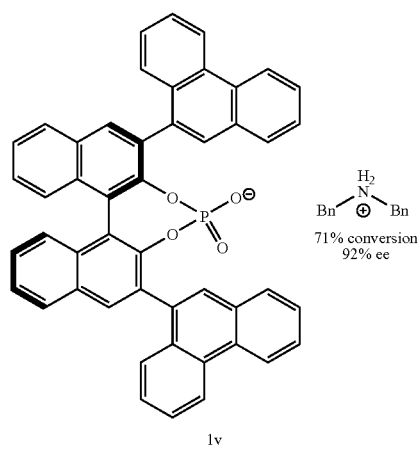

71% conversion
92% ee

1v

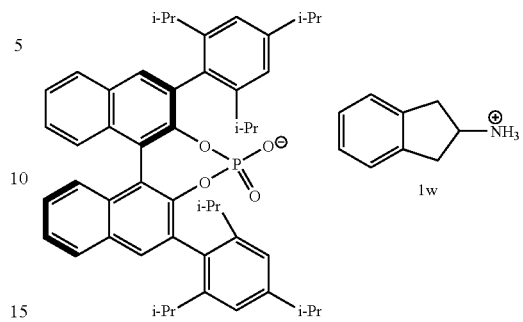

1w

Experimental Section

Preparation of the Salts

The acid (1 eq) in diethyl ether (2 ml/mmol) was initially charged and the particular amine (1 eq) was added in one portion. After stirring at room temperature for from 2 to 15 hours, the salt formed was filtered off or the solvent was evaporated off on a rotary evaporator. The salts were obtained in quantitative yields.

This reaction can be extended to the industrially important substance citral, which is reduced highly enantioselectively to the perfume ingredient citronellal (Scheme 10).

Scheme 10. Inventive highly enantioselective transfer hydrogenation of citral

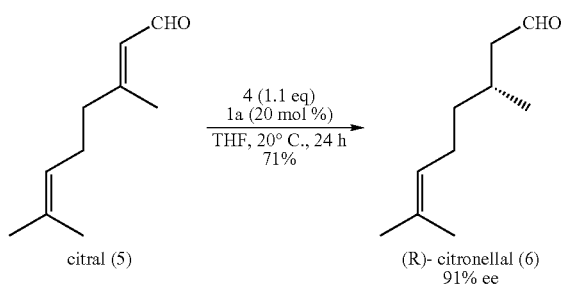

citral (5)

(R)- citronellal (6)
91% ee

Asymmetric Transfer Hydrogenation

The aldehyde (2a-f) (1 eq) and catalyst (1a-1w)) (0.2 eq for 1a, or 0.1 eq for 1b-1w) were initially charged in THF (aliphatic substrates) or 1,4-dioxane (aromatic substrates) (10 ml/mmol), and the mixture was stirred at room temperature (aliphatic substrates) or 50° C. (aromatic substrates) for 2-5 min. Thereafter, Hantzsch ester (4 or 5) was added and the mixture was stirred for a further 24 hours. The reaction mixture was supplemented with water (40 ml/mmol) and extracted with diethyl ether (aliphatic substrates) or methylene chloride (aromatic substrates) (3×40 ml/mmol). The combined organic phases were dried over magnesium sulfate and concentrated on a rotary evaporator.

Column chromatography (pentane/diethyl ether or hexane/ethyl acetate) gave the products in the yields and enantiomeric excesses reported.

For the examples shown in Schemes 7-9 and 11, a sample was taken and the conversion was determined by means of NMR.

Scheme 11. Inventive highly enantioselective transfer hydrogenation of an aliphatic substrate

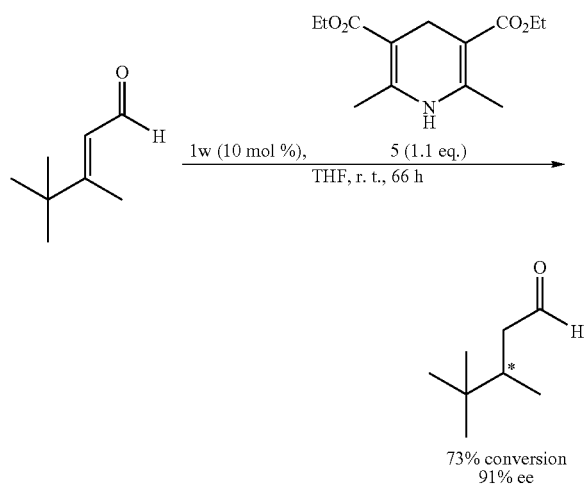

73% conversion
91% ee

Asymmetric Transfer Hydrogenation of α,β-Unsaturated Ketones (New Chapter)

The process can also be applied to α,β-unsaturated ketones. Especially chiral phosphate salts of primary amino acid esters have been found to be high performance and highly enantioselective catalysts.

For instance, the salt 7a, in the presence of the Hantzsch ester 8, catalyzes the highly enantioselective transfer hydrogenation of various α,β-unsaturated ketones (9) (Scheme 12).

Further catalytic salts for the enantioselective transfer hydrogenation are shown in Schemes 13-15.

Scheme 12.
Inventive highly enantioselective transfer hydrogenations.

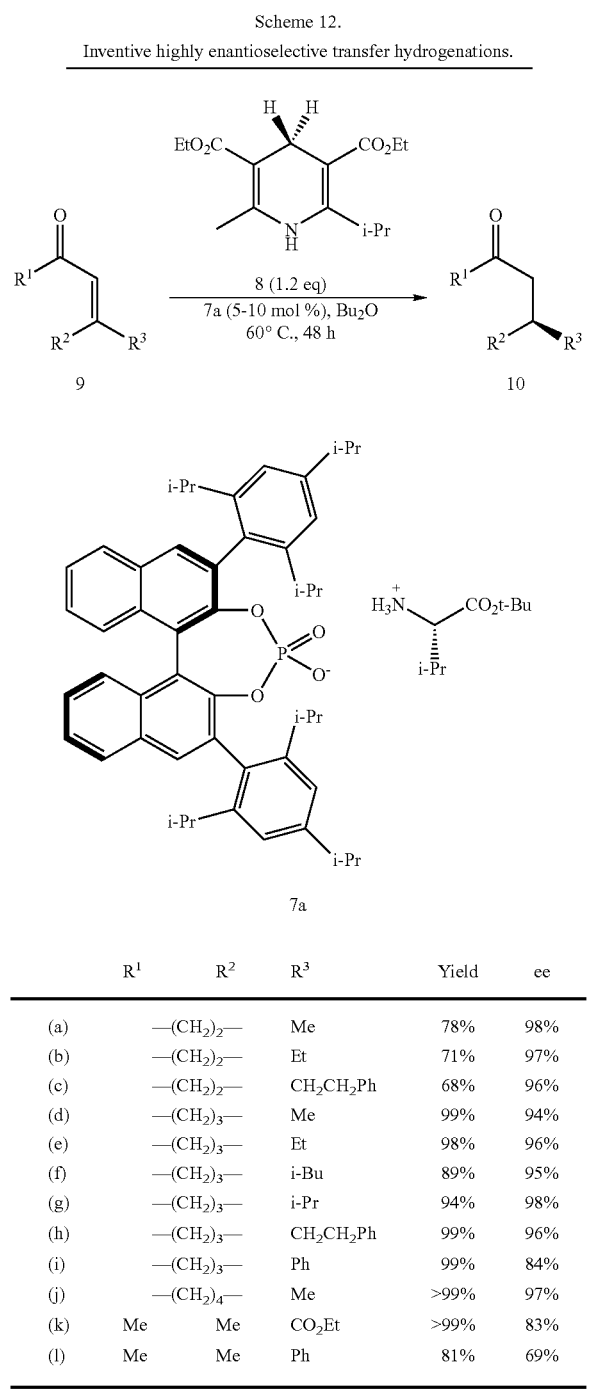

| | $R^1$ | $R^2$ | $R^3$ | Yield | ee |
|---|---|---|---|---|---|
| (a) | —$(CH_2)_2$— | | Me | 78% | 98% |
| (b) | —$(CH_2)_2$— | | Et | 71% | 97% |
| (c) | —$(CH_2)_2$— | | $CH_2CH_2Ph$ | 68% | 96% |
| (d) | —$(CH_2)_3$— | | Me | 99% | 94% |
| (e) | —$(CH_2)_3$— | | Et | 98% | 96% |
| (f) | —$(CH_2)_3$— | | i-Bu | 89% | 95% |
| (g) | —$(CH_2)_3$— | | i-Pr | 94% | 98% |
| (h) | —$(CH_2)_3$— | | $CH_2CH_2Ph$ | 99% | 96% |
| (i) | —$(CH_2)_3$— | | Ph | 99% | 84% |
| (j) | —$(CH_2)_4$— | | Me | >99% | 97% |
| (k) | Me | Me | $CO_2Et$ | >99% | 83% |
| (l) | Me | Me | Ph | 81% | 69% |

Scheme 13. Highly enantioselective transfer hydrogenation. Further examples of tert-butyl valinate salts.

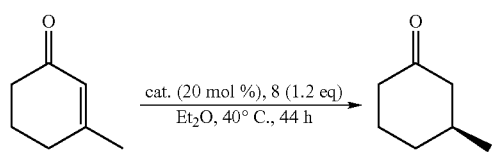

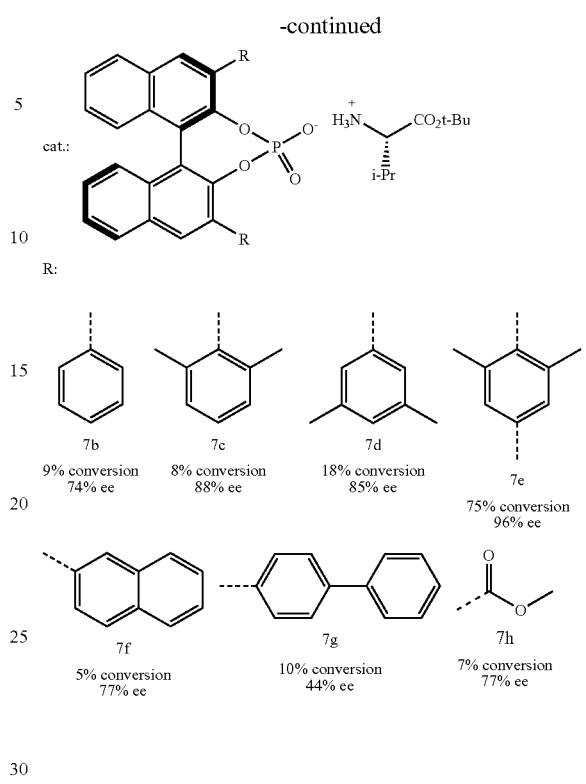

Scheme 14. Highly enantioselective transfer hydrogenation. Further examples of various 3,3′-bis(2,4,6-triisopropylphenyl)-1,1′-binaphthyl-2,2′diyl hydrogenphosphate salts.

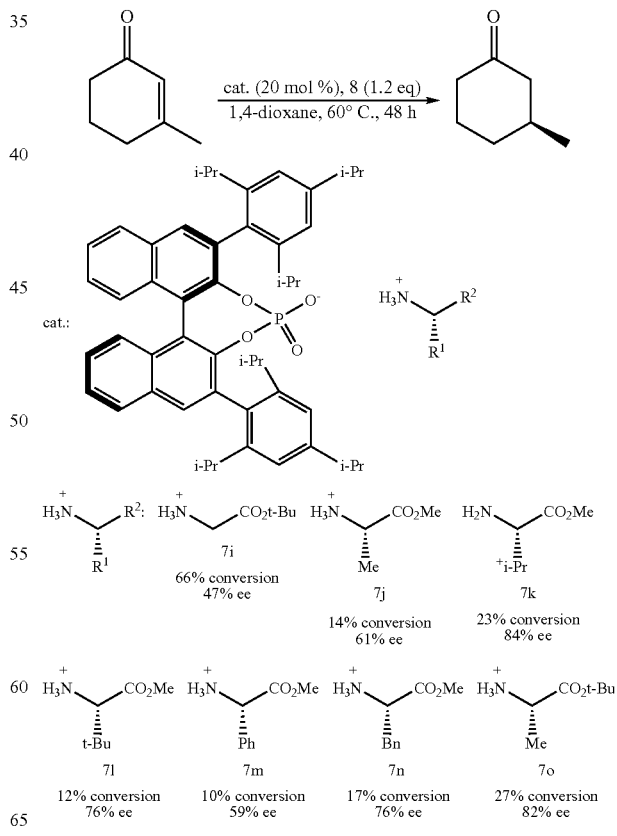

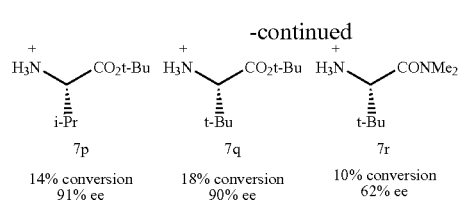

7p
14% conversion
91% ee 7q
18% conversion
90% ee 7r
10% conversion
62% ee

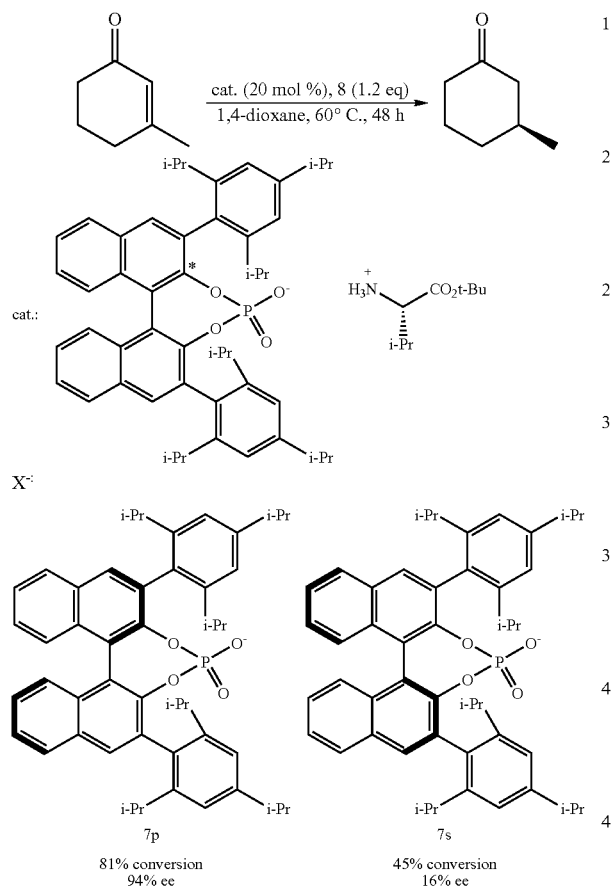

Scheme 15. Highly enantioselective transfer hydrogenation. Examples of the "match/mismatched" effect.

7p
81% conversion
94% ee 7s
45% conversion
16% ee

Experimental Section

Preparation of the Salts

The acid (1 eq) in diethyl ether (2 ml/mmol) was initially charged and the particular primary amine (1 eq) was added in one portion. After stirring at room temperature for from 2 to 15 hours, the salt formed was filtered off or the solvent was evaporated off on a rotary evaporator. The salts were obtained in quantitative yields.

Asymmetric Transfer Hydrogenation

The ketone (9a-l) (1 eq) and catalyst (7a-s) (0.1 eq for 9a-c, or 0.05 eq for 9d-l) were initially charged in $Bu_2O$ (0.33 ml/mmol), and the mixture was stirred at 60° C. for 2-5 min. Thereafter, Hantzsch ester (8) (1.2 eq) was added and the mixture was stirred for a further 48 hours. The reaction mixture was supplemented with sodium hydroxide solution (2N, 40 ml/mmol) and extracted with diethyl ether (3×40 ml/mmol). The combined organic phases were dried over magnesium sulfate and concentrated on a rotary evaporator. Column chromatography (pentane/diethyl ether) gave the products in the yields and enantiomeric excesses reported.

For the volatile saturated ketones, and also for the examples shown in Schemes 13-15, a sample was taken and the conversion was determined by means of GC.

Asymmetric Epoxidation

It is also possible to catalyze epoxidations in a manner analogous to Scheme 2. For example, cinnamaldehyde can be converted using tert-butyl hydroperoxide enantioselectively to the corresponding epoxide when the catalysts used are the salts 11 bw (Scheme 16).

Scheme 16.
Inventive highly enantioselective epoxidation

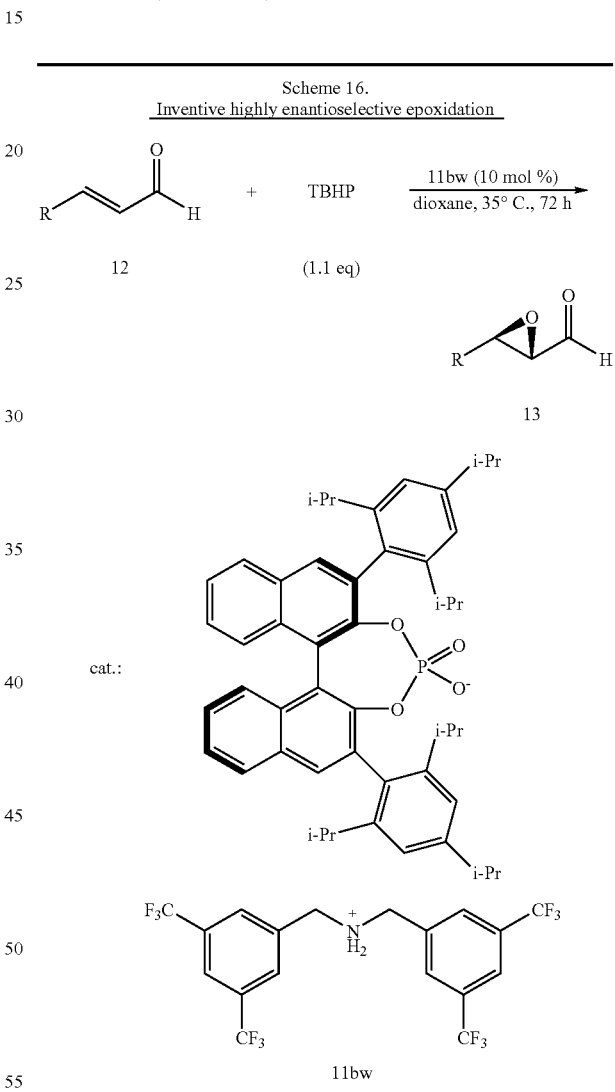

| | R | Yield | dr | ee |
|---|---|---|---|---|
| (a) | Ph | 75% | >99:1 | 91% |
| (b) | 2-naphthyl | 76% | >99:1 | 95% |
| (c) | 1-naphthyl | 70% | 98:2 | 91% |
| (d) | 4-Ph—$C_6H_4$ | 78% | >99:1 | 91% |
| (e) | 4-Me—$C_6H_4$ | 65% | >99:1 | 92% |
| (f) | 3-Me—$C_6H_4$ | 68% | >99:1 | 92% |
| (g) | 2-Me—$C_6H_4$ | 62% | 97:3 | 90% |
| (h) | 4-cyclohexyl-$C_6H_4$ | 60% | >99:1 | 90% |
| (i) | 4-F—$C_6H_4$ | 78% | >99:1 | 93% |
| (j) | 3-F—$C_6H_4$ | 82% | >99:1 | 84% |
| (k) | 2-F—$C_6H_4$ | 69% | 98:2 | 91% |

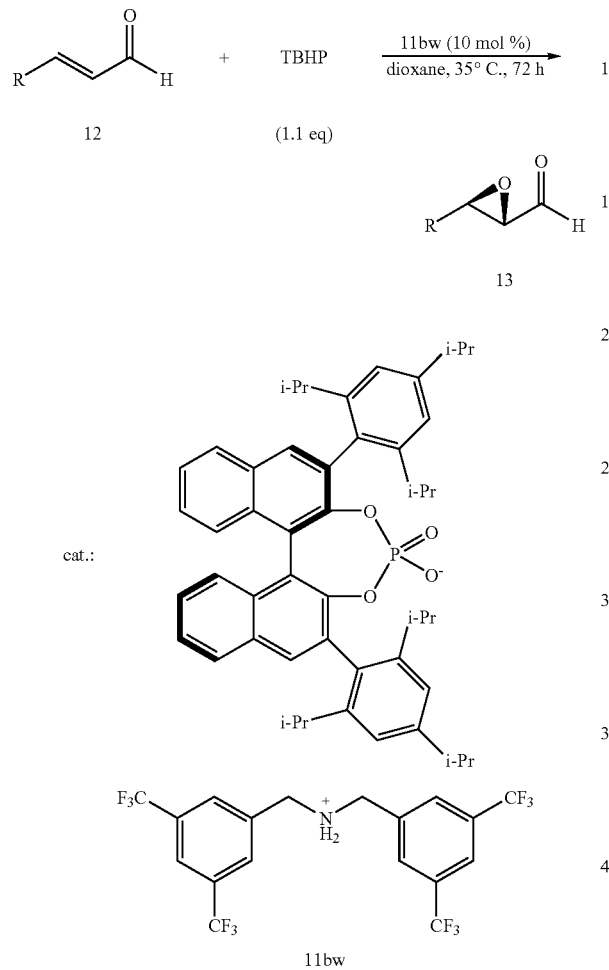
Scheme 16. Inventive highly enantioselective epoxidation
| R | Yield | dr | ee |
|---|---|---|---|
| (l) 4-Cl—C$_6$H$_4$ | 84% | >99:1 | 87% |
| (m) 4-Br—C$_6$H$_4$ | 80% | >99:1 | 87% |
| (n) n-hexyl | 92% | 95:5 | 70% |
Scheme 17. Highly enantioselective epoxidation. Further examples of various 3,3'-bis(2,4,6-triisopropylphenyl)-1,1'-binaphthyl-2,2'-diyl hydrogenphosphate salts with commercial achiral amines.
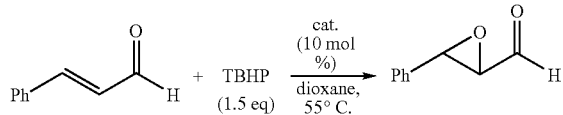
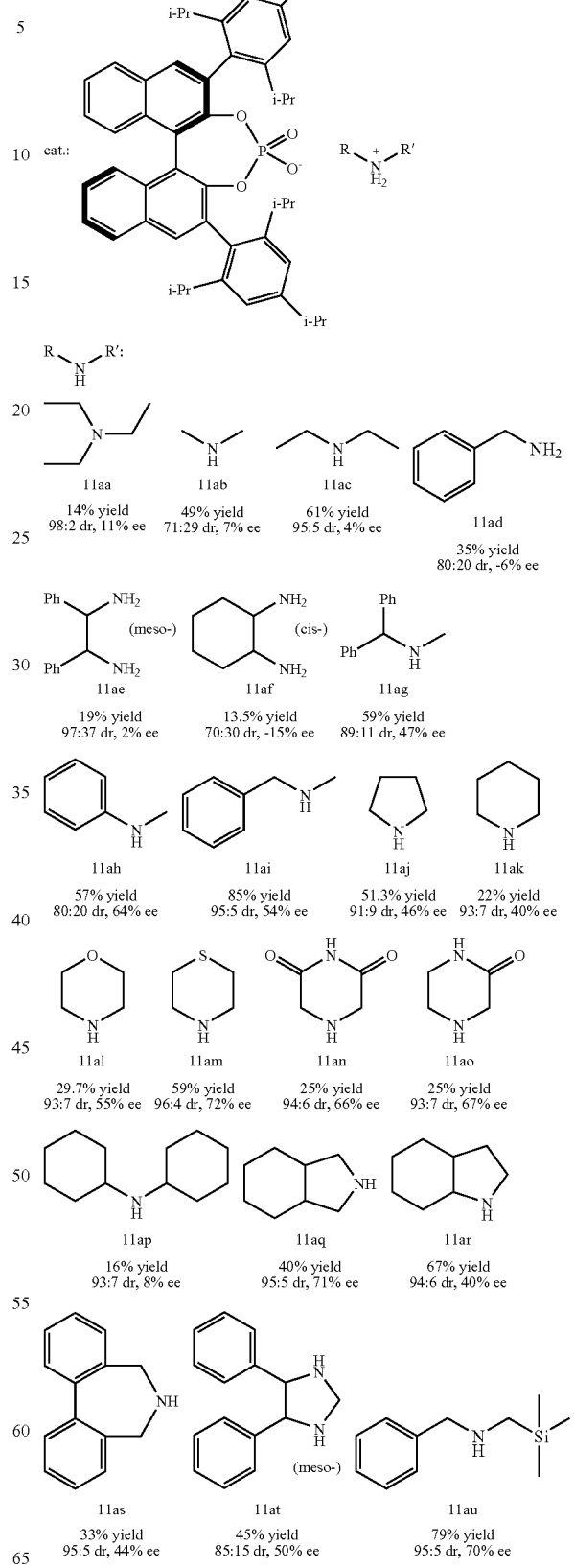

-continued
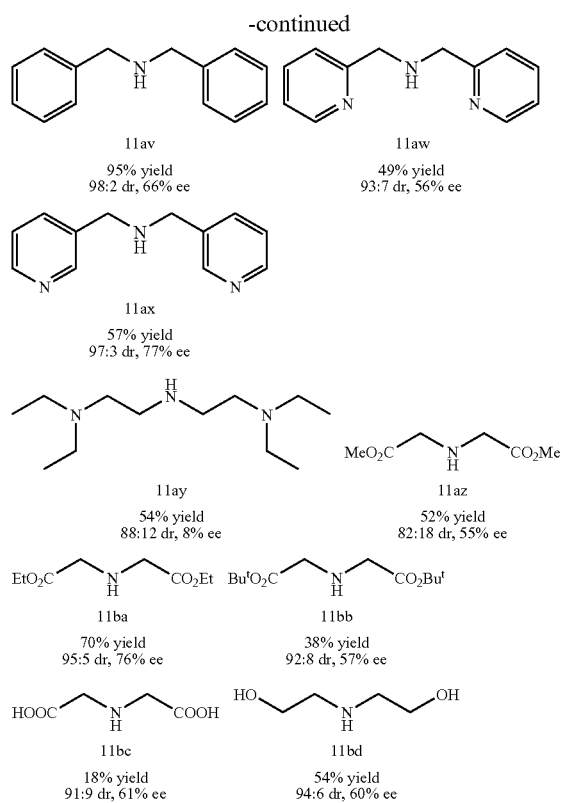
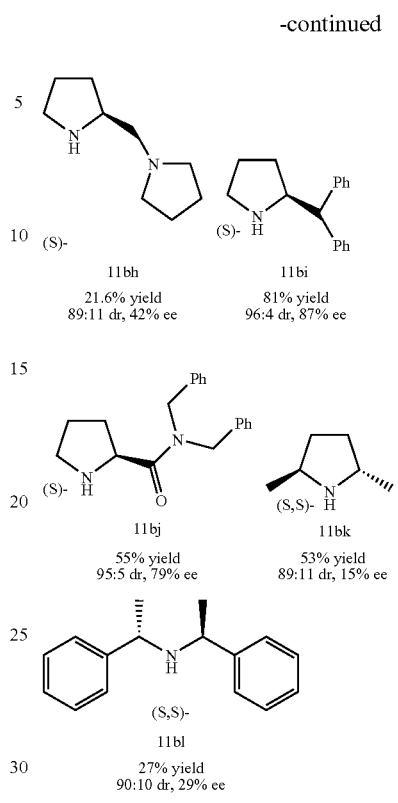
Scheme 18. Highly enantioselective epoxidation. Further examples of various 3,3′-bis(2,4,6-triisopropylphenyl)-1,1′-binaphthyl-2,2′-diyl hydrogenphosphate salts with chiral amines.
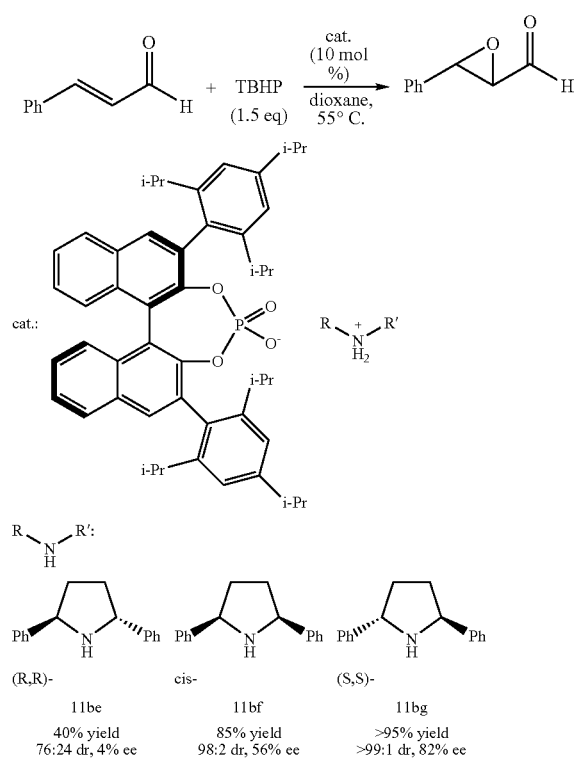
Scheme 19. Highly enantioselective epoxidation. Further examples of various 3,3′-bis(2,4,6-triisopropylphenyl)-1,1′-binaphthyl-2,2′-diyl hydrogenphosphate salts with benzoic hydrazides
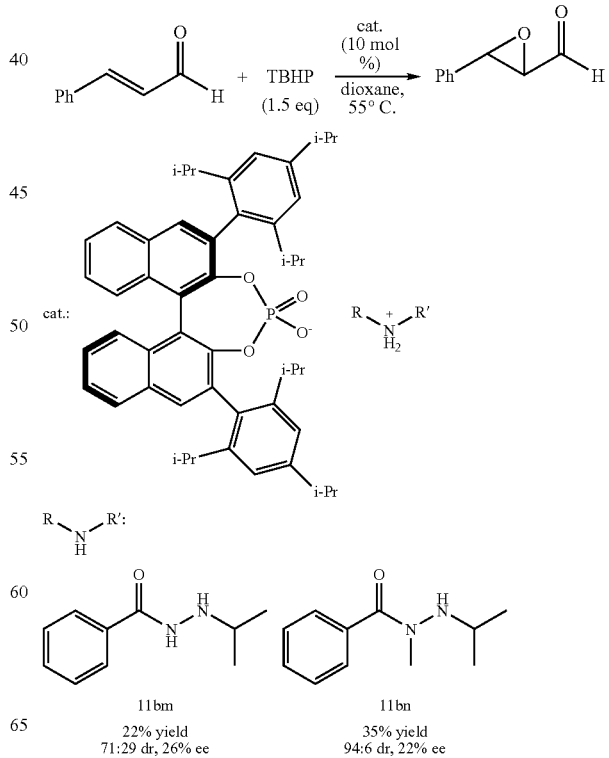

-continued

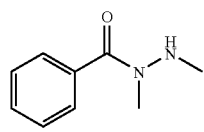

11bo
58% yield
93:7 dr, 73% ee

Scheme 20. Highly enantioselective epoxidation. Further examples of various 3,3′-bis(2,4,6-triisopropylphenyl)-1,1′-binaphthyl-2,2′-diyl hydrogenphosphate salts with dibenzylamines

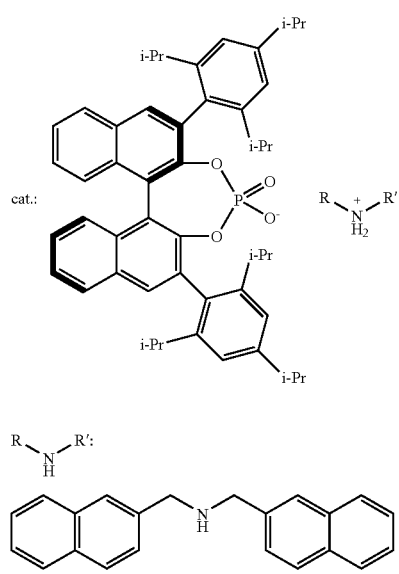

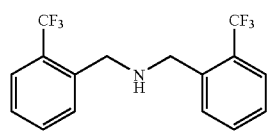

11bq
52% yield
96:4 dr, 59% ee

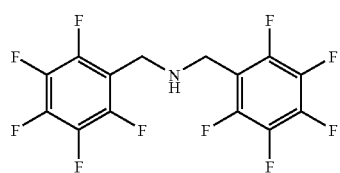

11br
25% yield
96:4 dr, 73% ee

-continued

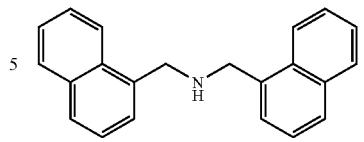

11bs
94% yield
97:3 dr, 66% ee

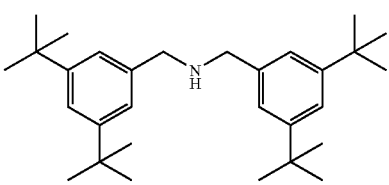

11bt
75% yield
94:6 dr, 55% ee

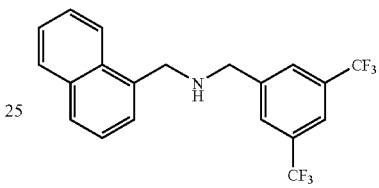

11bu
85% yield
98:2 dr, 83% ee

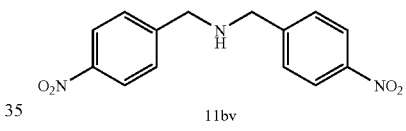

11bv
67% yield
97:3 dr, 78% ee

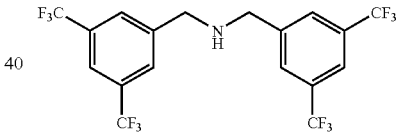

11bw
71% yield
>99:1 dr, 90% ee

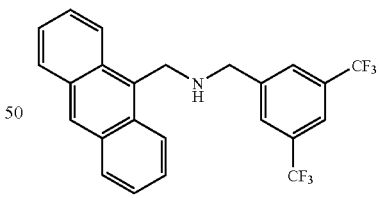

11bx
53% yield
98:2 dr, 64% ee

Scheme 21. Highly enantioselective epoxidation. Further examples of various dibenzylamine salts

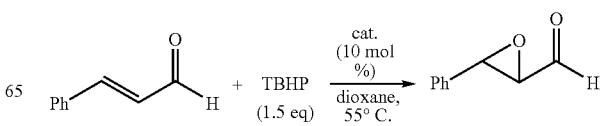

-continued
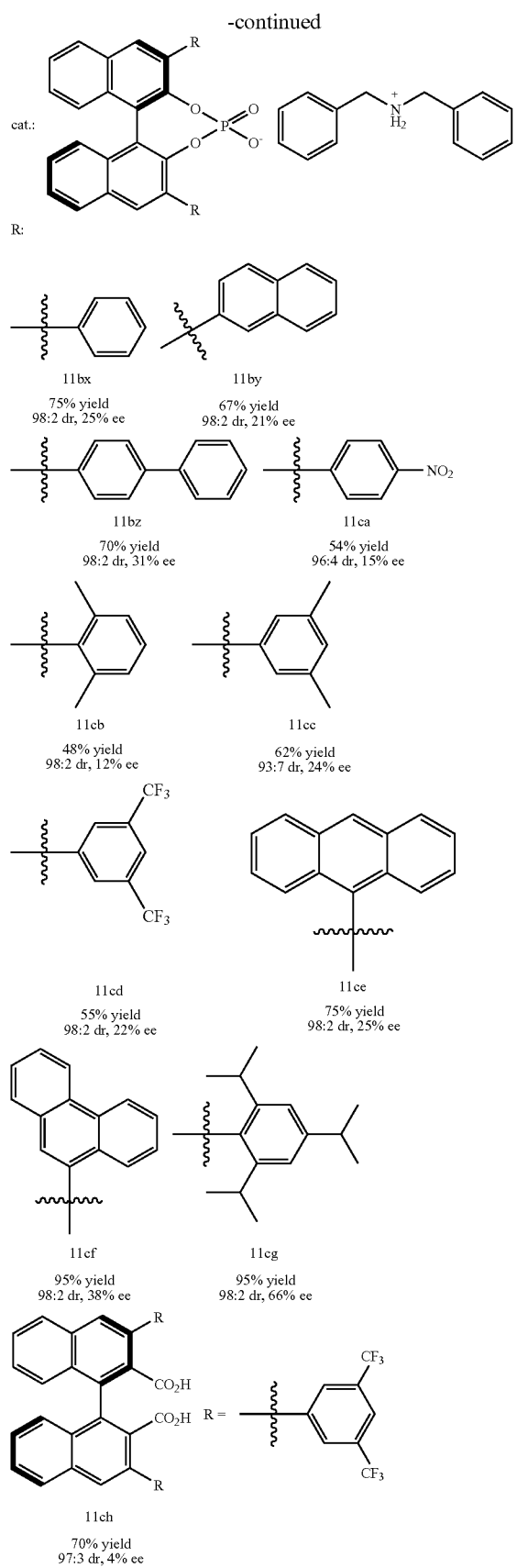
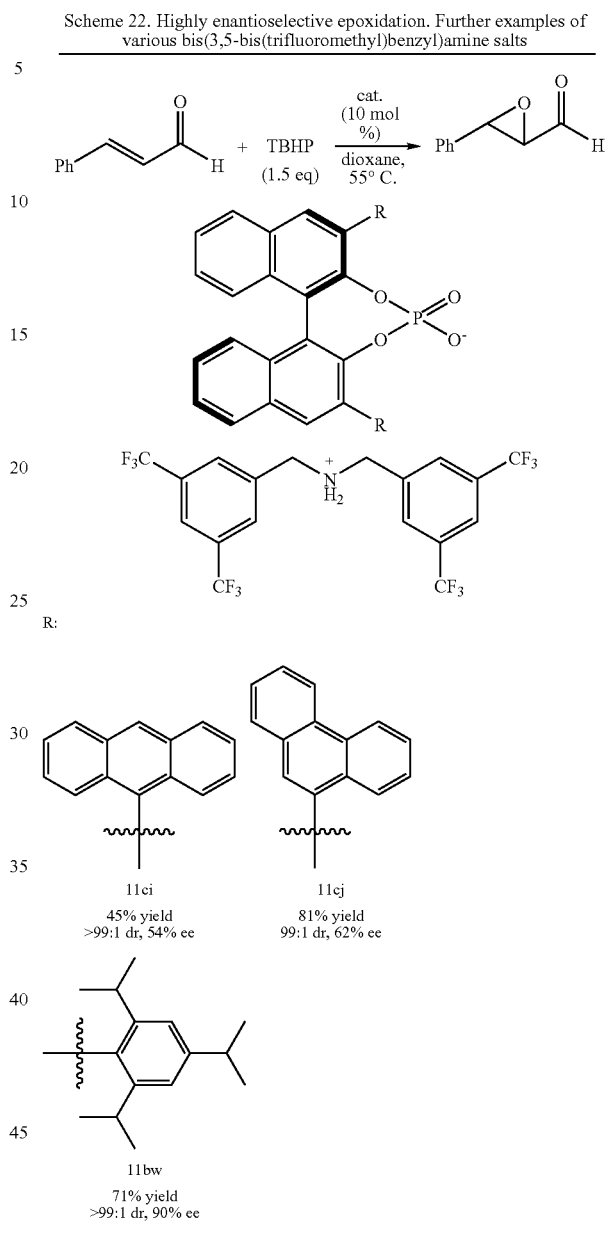
Scheme 22. Highly enantioselective epoxidation. Further examples of various bis(3,5-bis(trifluoromethyl)benzyl)amine salts
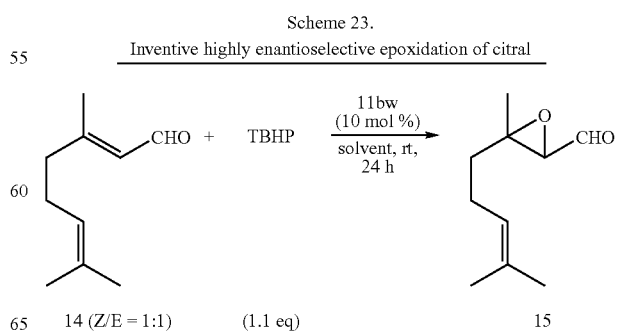
Scheme 23.
Inventive highly enantioselective epoxidation of citral

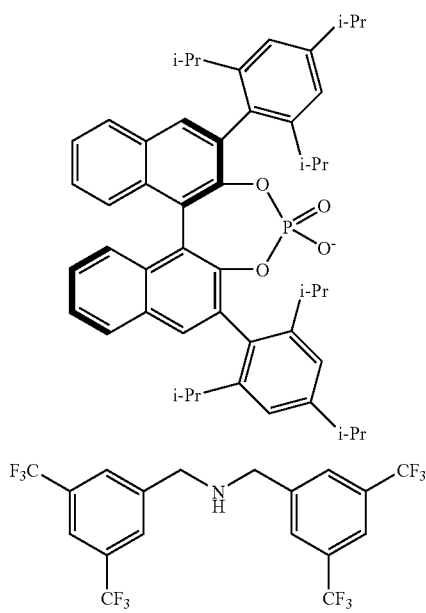

11bw

| | Solvent | Conversion | dr | ee |
|---|---|---|---|---|
| (a) | dioxane | 95% | 73:27 | 68%/89% |
| (b) | TBME | 95% | 72:28 | 76%/91% |
| (c) | Bu$_2$O | 95% | 78:22 | 81%/86% |
| (d) | Et$_2$O | 95% | 75:25 | 78%/90% |

Experimental Method:

Cinnamaldehyde (1 mmol) in dioxane (4 ml) is admixed with the catalyst (0.1 mmol, 10 mol %) and t-BuOOH (1.1 mmol, 1.1 eq), and the reaction mixture is stirred at 35° C. for 3 d. The reaction mixture was supplemented with a 10% NaHSO$_3$ solution (4 ml) and extracted with diethyl ether (3×4 ml). The combined organic phases were dried over magnesium sulfate and concentrated on a rotary evaporator.

Column chromatography affords the pure epoxide in the yields and ee's reported (Scheme 8).

Asymmetric Acyl Transfer Reaction

In accordance with Scheme 3, the novel catalysis strategy with chiral anions can also be extended to acyl transfer reactions. Reaction of α-phenylethanol with acetic anhydride in the presence of salts 9 and 10 takes place with clearly measurable enantioselectivity (Scheme 13).

Scheme 24. Inventive enantioselective esterification
Experimental method:

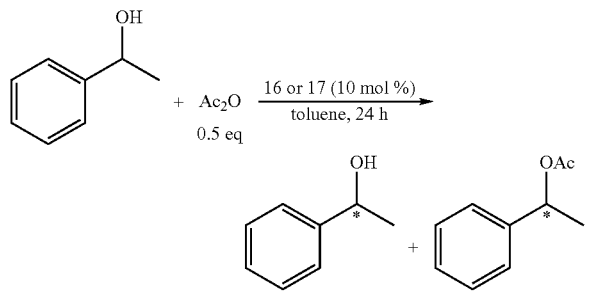

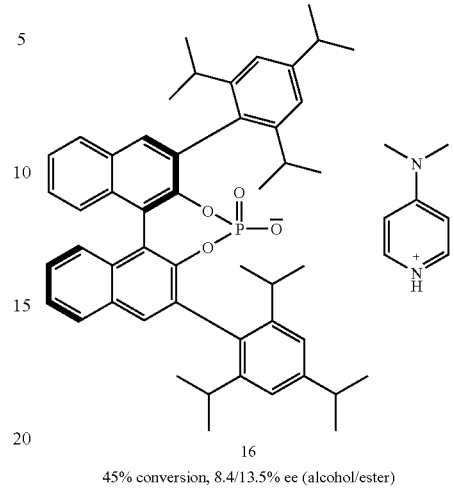

16
45% conversion, 8.4/13.5% ee (alcohol/ester)

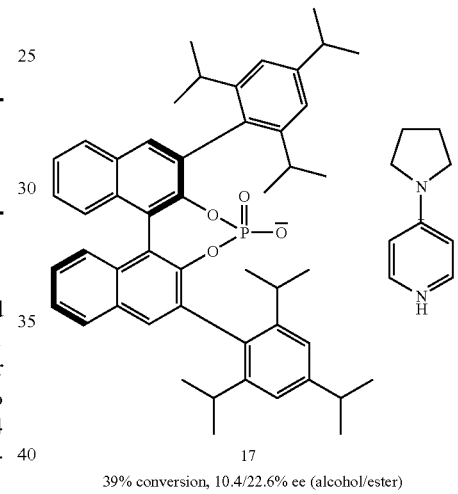

17
39% conversion, 10.4/22.6% ee (alcohol/ester)

The use of salt 16 is illustrative. For instance, the chiral phosphoric acid (TRIP, 7.53 mg, 0.01 mmol) and DMAP (1.22 mg, 0.01 mmol) in toluene (1 ml) is stirred for one hour. Subsequently, the racemic alcohol (0.1 mmol) and Ac$_2$O (0.05 mmol, 0.5 eq) are added. After the conversion reported, the product is isolated via aqueous workup.

The invention claimed is:

1. A process for preparing chiral organic compounds comprising conducting an asymmetric catalysis reaction that proceeds via cationic intermediates using an ionic catalyst, wherein the catalyst anion of the ionic catalyst is chiral and the catalyst cation is selected from the group consisting of NH$_4^+$, primary, secondary and tertiary ammonium salts, imidazol(in)ium salts, triazolium salts, amidinium salts, pyridinium salts, thiazol(in)ium salts, guanidinium salts, quarternary ammonium salts, and quaternary phosphonium salts.

2. The process as claimed in claim 1, wherein the catalyst anion is selected from the group consisting of chiral organic phosphates, sulfonates, sulfates, carboxylates, imides, and sulfonylimides.

3. The process as claimed in claim 1, wherein the anion derives from binaphthol.

4. The process as claimed in claim 1, wherein the anion is selected from

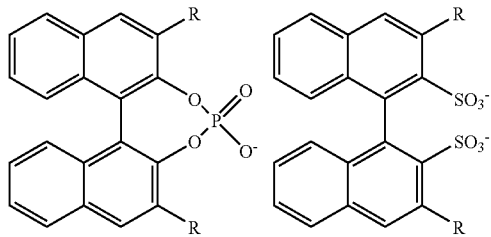

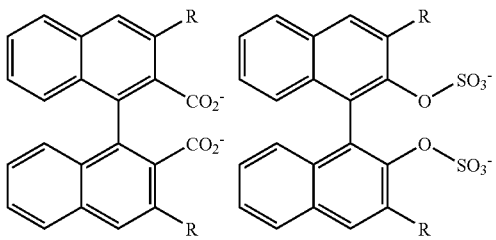

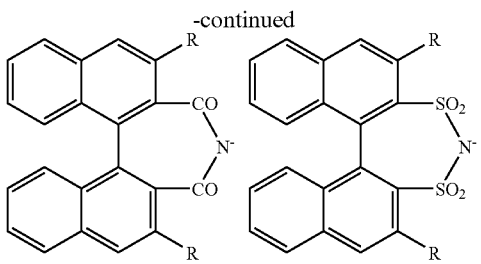

in which
R is hydrogen, substituted or unsubstituted alkyl or substituted or unsubstituted aryl.

5. The process as claimed in claim 1, wherein the cation is an ammonium compound.

6. The process as claimed in claim 1, wherein the reaction is selected from the group consisting of Diels-Alder reactions, 1,3-dipolar cycloadditions, conjugated additions, epoxidations, cyclopropanations, transfer hydrogenations, Mukaiyama-Michael additions, Knoevenagel reactions, and acryl transfer reactions.

* * * * *

UNITED STATES PATENT AND TRADEMARK OFFICE
CERTIFICATE OF CORRECTION

PATENT NO.       : 7,683,191 B2                                              Page 1 of 3
APPLICATION NO.  : 12/280821
DATED            : March 23, 2010
INVENTOR(S)      : List et al.

It is certified that error appears in the above-identified patent and that said Letters Patent is hereby corrected as shown below:

Title page:
(75) "Benjamin List, Mülheim an der Ruhr (DE); Sonja Mayer, Mülheim an der Ruhr (DE); Martin Nolwenn, Mulheim an der Ruhr (DE); Wang Xingwang, Mulheim an der Ruhr (DE)" should read -- Benjamin List, Mulheim an der Ruhr (DE); Sonja Mayer, Mulheim an der Ruhr (DE); Nolwenn Martin, Mülheim an der Ruhr (DE); Xingwang Wang, Mülheim an der Ruhr (DE) --

(73) "Studiangesellschaft Kohle mbH, Molhelm an der Ruhr (DE)" should read -- Studiengesellschaft Kohle mbH, Mülheim an der Ruhr (DE) --

Column 2, Line 47, "(a) chiral" should read -- (a)chiral --

Column 5, Line 55, "$SO_3$—" should read -- $SO_3^-$ --

Column 5, Line 56, "—COOH, —COO($C_1$-$C_6$-alkyl)" should read -- -COOH, -COO($C_1$-$C_6$-alkyl) --

Column 9, line 14,

"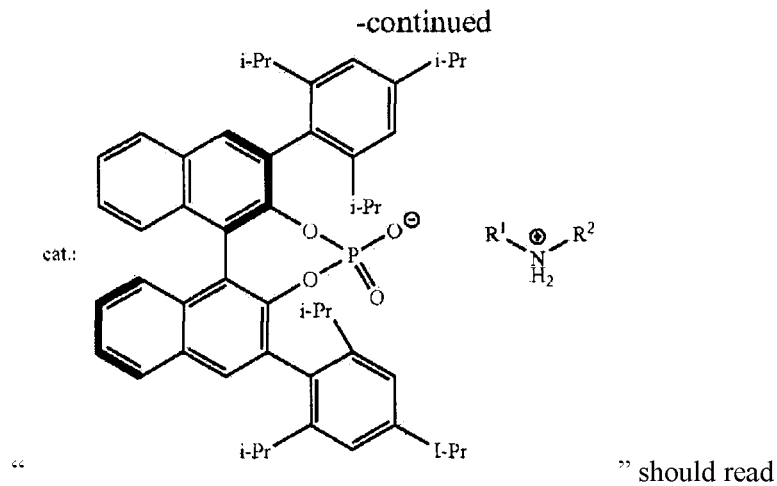" should read

Signed and Sealed this

Third Day of August, 2010

David J. Kappos
*Director of the United States Patent and Trademark Office*

CERTIFICATE OF CORRECTION (continued)
U.S. Pat. No. 7,683,191 B2

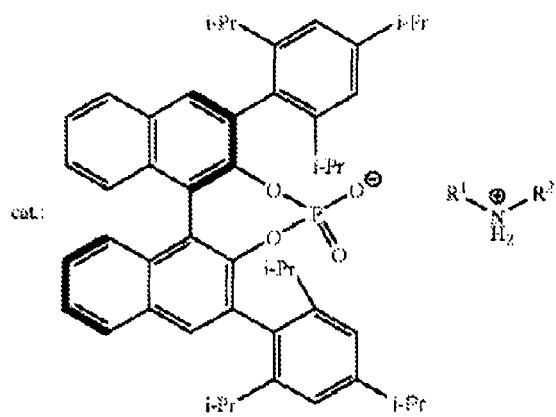

Column 18, line 50,

" 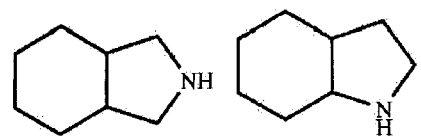 " should read

-- 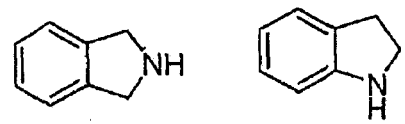 --

Column 25, line 9,

" 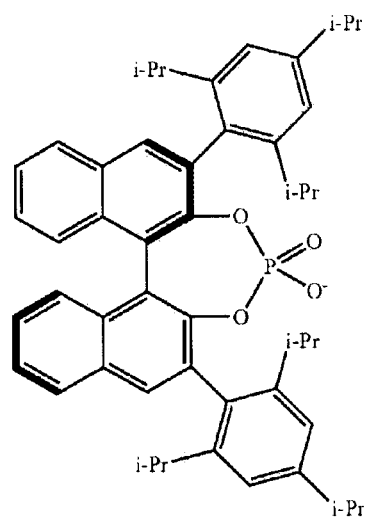 " should read

CERTIFICATE OF CORRECTION (continued)    Page 3 of 3
U.S. Pat. No. 7,683,191 B2

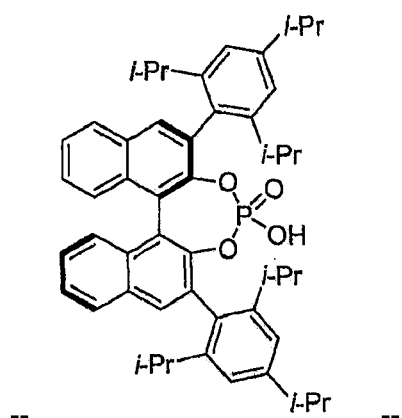

Column 26, line 34,

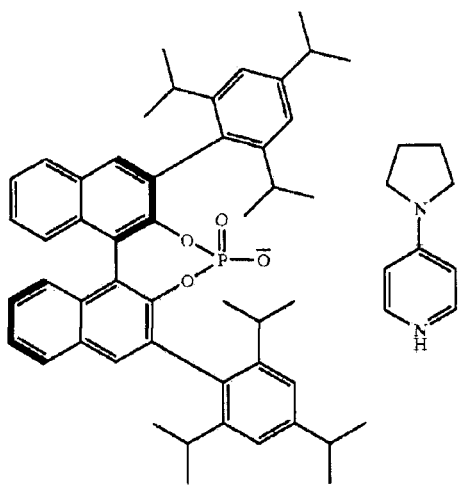

" should read

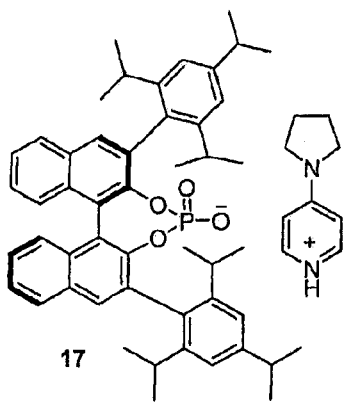

Column 26, Lines 57-58, "imidazol (in)ium" should read -- imidazol(in)ium --